(12) United States Patent
Conlon et al.

(10) Patent No.: US 10,143,454 B2
(45) Date of Patent: *Dec. 4, 2018

(54) LOADER FOR EXCHANGING END EFFECTORS IN VIVO

(71) Applicant: Ethicon Endo-Surgery, Inc., Cincinnati, OH (US)

(72) Inventors: Sean P. Conlon, Loveland, OH (US); James T. Spivey, Cincinnati, OH (US); Kevin M. Huey, Brea, CA (US); Rudolph H. Nobis, Mason, OH (US)

(73) Assignee: Ethicon LLC, Guaynabo, PR (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/081,179

(22) Filed: Mar. 25, 2016

(65) Prior Publication Data

US 2016/0206299 A1 Jul. 21, 2016

Related U.S. Application Data

(63) Continuation of application No. 12/576,565, filed on Oct. 9, 2009, now Pat. No. 9,295,485.

(51) Int. Cl.
*A61B 17/00* (2006.01)
*A61B 17/29* (2006.01)
(Continued)

(52) U.S. Cl.
CPC ........ *A61B 17/00234* (2013.01); *A61B 17/29* (2013.01); *A61B 17/3201* (2013.01);
(Continued)

(58) Field of Classification Search
CPC .............. A61B 17/00234; A61B 17/29; A61B 17/3201; A61B 18/1442;
(Continued)

(56) References Cited

U.S. PATENT DOCUMENTS 3,043,309 A 7/1962 McCarthy
3,358,676 A 12/1967 Frei et al.
(Continued)

FOREIGN PATENT DOCUMENTS

DE 10149421 A1 6/1905
EP 1709900 B1 10/2006
(Continued)

OTHER PUBLICATIONS

International Search Report dated Mar. 21, 2011, International Application No. PCT/US2010/051812.
(Continued)

*Primary Examiner* — Amy R Weisberg

(57) ABSTRACT

A surgical device for use in combination with a percutaneous elongate shaft defining a longitudinal axis. The shaft comprises a distal end and a proximal end, the distal end comprising an attachment mechanism. A surgical end effector is selectively attachable in vivo and detachable in vivo to the attachment mechanism of the percutaneous elongate shaft. A percutaneous elongate loader comprises an articulating distal end. The distal end comprises a tube with an opening at the distal tip, the tube being dimensioned to receive the surgical end effector. The distal end further comprises an engagement feature capable of frictionally holding the surgical end effector in the tube during in vivo attachment to and in vivo detachment from the percutaneous elongate shaft.

6 Claims, 11 Drawing Sheets

(51) Int. Cl.
 *A61B 17/32* (2006.01)
 *A61B 17/3201* (2006.01)
 *A61B 18/14* (2006.01)

(52) U.S. Cl.
 CPC .. *A61B 17/320092* (2013.01); *A61B 18/1442* (2013.01); *A61B 2017/00238* (2013.01); *A61B 2017/00296* (2013.01); *A61B 2017/00464* (2013.01); *A61B 2017/00473* (2013.01); *A61B 2017/00477* (2013.01); *A61B 2018/1495* (2013.01)

(58) Field of Classification Search
 CPC .. A61B 17/320092; A61B 2017/00477; A61B 2017/00238; A61B 2017/00464; A61B 2018/1495; A61B 2017/00296; A61B 2017/00473
 See application file for complete search history.

(56) References Cited

U.S. PATENT DOCUMENTS

| | | |
|---|---|---|
| 3,710,399 A | 1/1973 | Hurst |
| 3,893,448 A | 7/1975 | Brantigan |
| 3,906,217 A | 9/1975 | Lackore |
| 3,988,535 A | 10/1976 | Hickman et al. |
| 4,047,136 A | 9/1977 | Satto |
| 4,063,561 A | 12/1977 | McKenna |
| 4,099,192 A | 7/1978 | Aizawa et al. |
| 4,278,077 A | 7/1981 | Mizumoto |
| 4,384,584 A | 5/1983 | Chen |
| 4,585,282 A | 4/1986 | Bosley |
| 4,597,390 A | 7/1986 | Mulhollan et al. |
| 4,655,746 A | 4/1987 | Daniels et al. |
| 5,052,402 A | 10/1991 | Bencini et al. |
| 5,053,043 A | 10/1991 | Gottesman et al. |
| 5,201,743 A | 4/1993 | Haber et al. |
| 5,282,806 A | 2/1994 | Haber et al. |
| 5,286,255 A | 2/1994 | Weber |
| 5,308,357 A | 5/1994 | Lichtman |
| 5,314,424 A | 5/1994 | Nicholas |
| 5,330,502 A | 7/1994 | Hassler et al. |
| 5,352,219 A | 10/1994 | Reddy |
| 5,392,917 A | 2/1995 | Alpem et al. |
| 5,417,203 A | 5/1995 | Tovey et al. |
| 5,441,059 A | 8/1995 | Dannan |
| 5,468,250 A | 11/1995 | Paraschac et al. |
| 5,502,698 A | 3/1996 | Mochizuki |
| 5,507,297 A | 4/1996 | Slater et al. |
| 5,507,774 A | 4/1996 | Homes et al. |
| 5,540,648 A | 7/1996 | Yoon |
| 5,562,655 A | 10/1996 | Mittelstadt et al. |
| 5,578,052 A | 11/1996 | Koros et al. |
| 5,593,402 A | 1/1997 | Patrick |
| 5,613,937 A | 3/1997 | Garrison et al. |
| 5,618,303 A | 4/1997 | Marlow et al. |
| 5,632,764 A | 5/1997 | Beideman et al. |
| 5,704,534 A * | 1/1998 | Huitema ............ A61B 17/07207 227/175.1 |
| 5,716,326 A | 2/1998 | Dannan |
| 5,718,714 A | 2/1998 | Livneh |
| 5,722,988 A | 3/1998 | Weisshaupt |
| 5,762,255 A | 6/1998 | Chrisman et al. |
| 5,782,748 A | 7/1998 | Palmer et al. |
| 5,792,165 A | 8/1998 | Klieman et al. |
| 5,810,865 A | 9/1998 | Koscher et al. |
| 5,810,877 A | 9/1998 | Roth et al. |
| 5,881,615 A * | 3/1999 | Dahl ..................... B25G 1/085 16/111.1 |
| 5,893,875 A | 4/1999 | O'Connor et al. |
| 5,928,263 A | 7/1999 | Hoogeboom |
| 5,980,455 A | 11/1999 | Daniel et al. |
| 6,024,748 A | 2/2000 | Mazo et al. |
| 6,059,719 A | 5/2000 | Yamamoto et al. |
| 6,099,537 A | 8/2000 | Sugai et al. |
| 6,126,359 A | 10/2000 | Dittrich et al. |
| 6,159,200 A | 12/2000 | Verdura et al. |
| 6,273,882 B1 | 8/2001 | Whittier et al. |
| 6,309,397 B1 | 10/2001 | Julian et al. |
| 6,315,789 B1 | 11/2001 | Cragg |
| 6,419,688 B1 | 7/2002 | Bacher et al. |
| 6,471,172 B1 | 10/2002 | Lemke et al. |
| 6,589,211 B1 | 7/2003 | MacLeod |
| 6,595,984 B1 | 7/2003 | DeGuillebon |
| 6,626,824 B2 | 9/2003 | Ruegg et al. |
| 6,635,071 B2 | 10/2003 | Boche et al. |
| 6,663,641 B1 | 12/2003 | Kovac et al. |
| 6,666,875 B1 | 12/2003 | Sakurai et al. |
| 6,723,043 B2 | 4/2004 | Kleeman et al. |
| 6,770,081 B1 | 8/2004 | Cooper et al. |
| 6,776,165 B2 | 8/2004 | Jin |
| 6,814,742 B2 | 11/2004 | Kimura et al. |
| 6,827,712 B2 | 12/2004 | Tovey et al. |
| 6,860,878 B2 | 3/2005 | Brock |
| 6,869,395 B2 | 3/2005 | Page et al. |
| 6,884,213 B2 | 4/2005 | Raz et al. |
| 6,916,314 B2 | 7/2005 | Schneider et al. |
| 6,936,003 B2 | 8/2005 | Iddan |
| 6,942,674 B2 | 9/2005 | Belef et al. |
| 6,986,738 B2 | 1/2006 | Glukhovsky et al. |
| 6,994,708 B2 | 2/2006 | Manzo et al. |
| 7,039,453 B2 | 5/2006 | Mullick et al. |
| 7,042,184 B2 | 5/2006 | Oleynikov et al. |
| 7,066,879 B2 | 6/2006 | Fowler et al. |
| 7,083,579 B2 | 8/2006 | Yokoi et al. |
| 7,122,028 B2 | 10/2006 | Looper et al. |
| 7,125,403 B2 | 10/2006 | Julian et al. |
| 7,169,104 B2 | 1/2007 | Ueda et al. |
| 7,199,545 B2 | 4/2007 | Oleynikov et al. |
| 7,211,094 B2 | 5/2007 | Gannoe et al. |
| 7,241,290 B2 | 7/2007 | Doyle et al. |
| 7,297,142 B2 | 11/2007 | Brock |
| 7,331,967 B2 | 2/2008 | Lee et al. |
| 7,429,259 B2 | 9/2008 | Cadeddu et al. |
| 7,448,993 B2 | 11/2008 | Yokoi et al. |
| 7,559,887 B2 | 7/2009 | Dannan |
| 7,566,331 B2 | 7/2009 | Looper et al. |
| 7,604,642 B2 | 10/2009 | Brock |
| 7,651,471 B2 | 1/2010 | Yokoi et al. |
| 7,666,181 B2 * | 2/2010 | Abou El Kheir .. A61B 17/3421 600/104 |
| 7,678,043 B2 | 3/2010 | Gilad |
| 7,691,103 B2 | 4/2010 | Fernandez et al. |
| 7,691,126 B2 | 4/2010 | Bacher |
| 7,699,835 B2 | 4/2010 | Lee et al. |
| 7,722,599 B2 | 5/2010 | Julian et al. |
| 7,841,980 B2 | 11/2010 | Minosawa et al. |
| 7,862,553 B2 | 1/2011 | Ewaschuk |
| 7,894,882 B2 | 2/2011 | Mullick et al. |
| 7,901,398 B2 | 3/2011 | Stanczak et al. |
| 8,012,154 B2 | 9/2011 | Livneh |
| 8,021,358 B2 | 9/2011 | Doyle et al. |
| 8,038,612 B2 | 10/2011 | Paz |
| 8,052,636 B2 | 11/2011 | Moll et al. |
| 8,057,502 B2 | 11/2011 | Maliglowka et al. |
| 8,088,062 B2 | 1/2012 | Zwolinski |
| 8,114,098 B2 | 2/2012 | Kimura et al. |
| 8,128,643 B2 | 3/2012 | Aranyi et al. |
| 8,133,254 B2 | 3/2012 | Dumbauld et al. |
| 8,182,414 B2 | 5/2012 | Handa et al. |
| 8,187,166 B2 | 5/2012 | Kuth et al. |
| 8,353,897 B2 | 1/2013 | Doyle et al. |
| 8,377,044 B2 | 2/2013 | Coe et al. |
| 8,397,335 B2 | 3/2013 | Gordin et al. |
| 8,398,544 B2 | 3/2013 | Altamirano |
| 8,409,076 B2 | 4/2013 | Pang et al. |
| 8,475,361 B2 | 7/2013 | Barlow et al. |
| 8,518,024 B2 | 8/2013 | Williams et al. |
| 8,545,519 B2 | 10/2013 | Aguirre et al. |
| 8,623,011 B2 | 1/2014 | Spivey |
| 8,636,648 B2 | 1/2014 | Gazdzinski |
| 8,721,529 B2 | 5/2014 | Hess et al. |
| 8,721,539 B2 | 5/2014 | Shohat et al. |
| 8,747,394 B2 | 6/2014 | Belson et al. |

(56) References Cited

U.S. PATENT DOCUMENTS

| | | |
|---|---|---|
| 8,758,391 B2 | 6/2014 | Swayze et al. |
| 8,764,735 B2 | 7/2014 | Coe et al. |
| 8,845,661 B2 | 9/2014 | D'Arcangelo et al. |
| 8,939,997 B2 | 1/2015 | Martinez et al. |
| 8,979,891 B2 | 3/2015 | McLawhorn et al. |
| 9,061,562 B2 | 6/2015 | Hayakawa |
| 9,125,681 B2 | 9/2015 | Parihar et al. |
| 9,186,203 B2 | 11/2015 | Spivey et al. |
| 9,295,485 B2 | 3/2016 | Conlon et al. |
| 9,451,937 B2 | 9/2016 | Parihar |
| 9,526,516 B2 | 12/2016 | Parihar et al. |
| 9,662,132 B2 | 5/2017 | Coe et al. |
| 2001/0051766 A1 | 12/2001 | Gazdzinski |
| 2002/0128645 A1 | 9/2002 | Messerly |
| 2002/0177843 A1 | 11/2002 | Anderson et al. |
| 2003/0114731 A1 | 6/2003 | Cadeddu et al. |
| 2004/0093039 A1 | 5/2004 | Schumert |
| 2004/0152941 A1 | 8/2004 | Asmus et al. |
| 2004/0267254 A1 | 12/2004 | Manzo et al. |
| 2005/0033354 A1 | 2/2005 | Montalvo et al. |
| 2005/0119640 A1 | 6/2005 | Sverduk et al. |
| 2005/0131396 A1 | 6/2005 | Stanczak et al. |
| 2005/0131457 A1 | 6/2005 | Douglas et al. |
| 2005/0215983 A1 | 9/2005 | Brock |
| 2005/0250984 A1 | 11/2005 | Lam et al. |
| 2005/0272972 A1 | 12/2005 | Iddan |
| 2005/0272974 A1 | 12/2005 | Iddan |
| 2005/0273139 A1 | 12/2005 | Krauss et al. |
| 2005/0288555 A1 | 12/2005 | Binmoeller |
| 2006/0079933 A1 | 4/2006 | Hushka et al. |
| 2006/0184161 A1 | 8/2006 | Maahs et al. |
| 2006/0190035 A1 | 8/2006 | Hushka et al. |
| 2006/0258905 A1 | 11/2006 | Kaji et al. |
| 2007/0010709 A1 | 1/2007 | Reinschke |
| 2007/0049966 A1 | 3/2007 | Bonadio et al. |
| 2007/0073247 A1 | 3/2007 | Ewaschuk |
| 2007/0093792 A1 | 4/2007 | Julian et al. |
| 2007/0123748 A1 | 5/2007 | Meglan |
| 2007/0270651 A1 | 11/2007 | Gilad et al. |
| 2008/0004656 A1 | 1/2008 | Livneh |
| 2008/0015413 A1 | 1/2008 | Barlow et al. |
| 2008/0015552 A1 | 1/2008 | Doyle et al. |
| 2008/0045003 A1 | 2/2008 | Lee et al. |
| 2008/0140090 A1 | 6/2008 | Aranyi et al. |
| 2008/0142005 A1 | 6/2008 | Schnell |
| 2008/0154299 A1 | 6/2008 | Livneh |
| 2008/0242939 A1 | 10/2008 | Johnson |
| 2008/0243106 A1 | 10/2008 | Coe et al. |
| 2008/0287926 A1 | 11/2008 | Abou El Kheir |
| 2009/0005638 A1 | 1/2009 | Zwolinski |
| 2009/0171147 A1 | 7/2009 | Lee et al. |
| 2009/0209947 A1 | 8/2009 | Gordin et al. |
| 2010/0198248 A1 | 8/2010 | Vakharia |
| 2010/0249700 A1 | 9/2010 | Spivey |
| 2011/0040322 A1 | 2/2011 | Major |
| 2011/0087265 A1 | 4/2011 | Nobis et al. |
| 2011/0087266 A1 | 4/2011 | Conlon et al. |
| 2011/0087267 A1 | 4/2011 | Spivey et al. |
| 2011/0115891 A1 | 5/2011 | Trusty |
| 2011/0208007 A1 | 8/2011 | Shohat et al. |
| 2011/0230869 A1 | 9/2011 | Altamirano |
| 2011/0288560 A1 | 11/2011 | Shohat et al. |
| 2012/0053402 A1 | 3/2012 | Conlon et al. |
| 2012/0053406 A1 | 3/2012 | Conlon et al. |
| 2012/0065627 A1 | 3/2012 | Ghabrial et al. |
| 2012/0078290 A1 | 3/2012 | Nobis et al. |
| 2012/0078291 A1 | 3/2012 | Nobis et al. |
| 2012/0083778 A1 | 4/2012 | McGaffigan et al. |
| 2012/0083826 A1 | 4/2012 | Chao et al. |
| 2012/0088965 A1 | 4/2012 | Stokes et al. |
| 2012/0089093 A1 | 4/2012 | Trusty |
| 2012/0095298 A1 | 4/2012 | Stefanchik et al. |
| 2012/0259325 A1 | 10/2012 | Houser et al. |
| 2012/0289773 A1 | 11/2012 | Joshi et al. |
| 2012/0316575 A1 | 12/2012 | Farin et al. |
| 2014/0005474 A1 | 1/2014 | Farin et al. |
| 2014/0066711 A1 | 3/2014 | Farin et al. |
| 2014/0088637 A1 | 3/2014 | Parihar et al. |
| 2014/0088638 A1 | 3/2014 | Parihar |
| 2014/0243799 A1 | 8/2014 | Parihar |
| 2014/0243800 A1 | 8/2014 | Parihar |
| 2014/0277018 A1 | 9/2014 | Parihar |
| 2015/0088191 A1 | 3/2015 | Coe et al. |

FOREIGN PATENT DOCUMENTS

| | | |
|---|---|---|
| EP | 2485632 B1 | 4/2016 |
| JP | 2005261734 A | 9/2005 |
| JP | 5770194 B2 | 7/2015 |
| WO | WO 2008/015666 A2 | 2/2008 |
| WO | WO 2010/114634 A1 | 10/2010 |
| WO | WO 2011/044353 A1 | 4/2011 |
| WO | WO 2012/035524 A2 | 3/2012 |
| WO | WO 2012/040183 A1 | 3/2012 |
| WO | WO 2012/112622 A3 | 8/2012 |
| WO | WO 2012/126967 A2 | 9/2012 |
| WO | WO 2013/007764 A2 | 1/2013 |
| WO | WO 2013/048963 A2 | 4/2013 |
| WO | WO 2014/052177 A1 | 4/2014 |

OTHER PUBLICATIONS

International Search Report dated Dec. 12, 2011, International Application No. PCT/US2011/05237.

International Preliminary Report dated Apr. 11, 2012; International Application No. PCT/US2010/051812.

International Search Report dated Mar. 2, 2012; International Application No. PCT/US2011/050198.

International Preliminary Search Report dated Mar. 5, 2013; International Application No. PCT/US2011/050198.

International Preliminary Report dated Mar. 26, 2013; International Application No. PCT/US2011/052327.

International Search Report, dated Apr. 3, 2013; International Application No. PCT/US2012/056900.

International Search Report dated Dec. 20, 2013; International Application No. PCT/US2013/060803.

International Preliminary Report dated Apr. 1, 2014; International Application No. PCT/US2012/056900.

International Search Report dated May 28, 2014; International Application No. PCT/US2014/015738.

International Search Report dated Mar. 31, 2015; International Application No. PCT/US2013/060803.

International Preliminary Search Report dated Sep. 1, 2015, International Application No. PCT/US2014/015738.

* cited by examiner

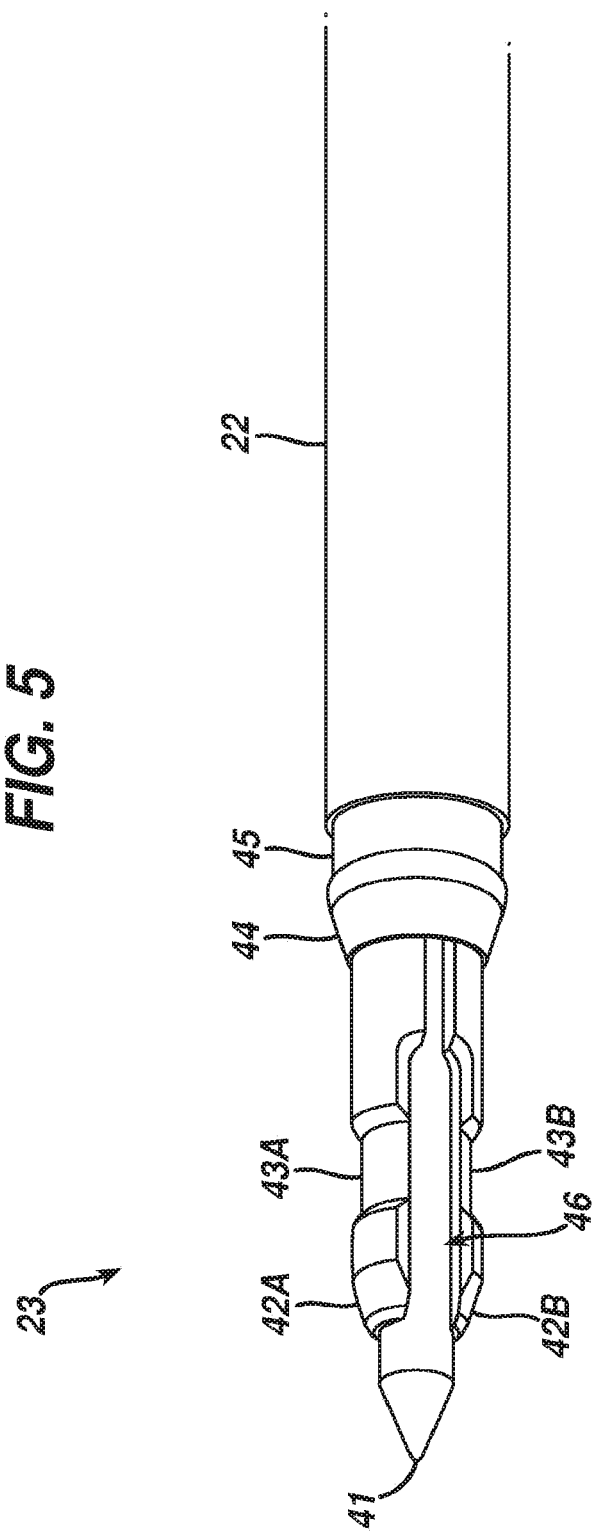

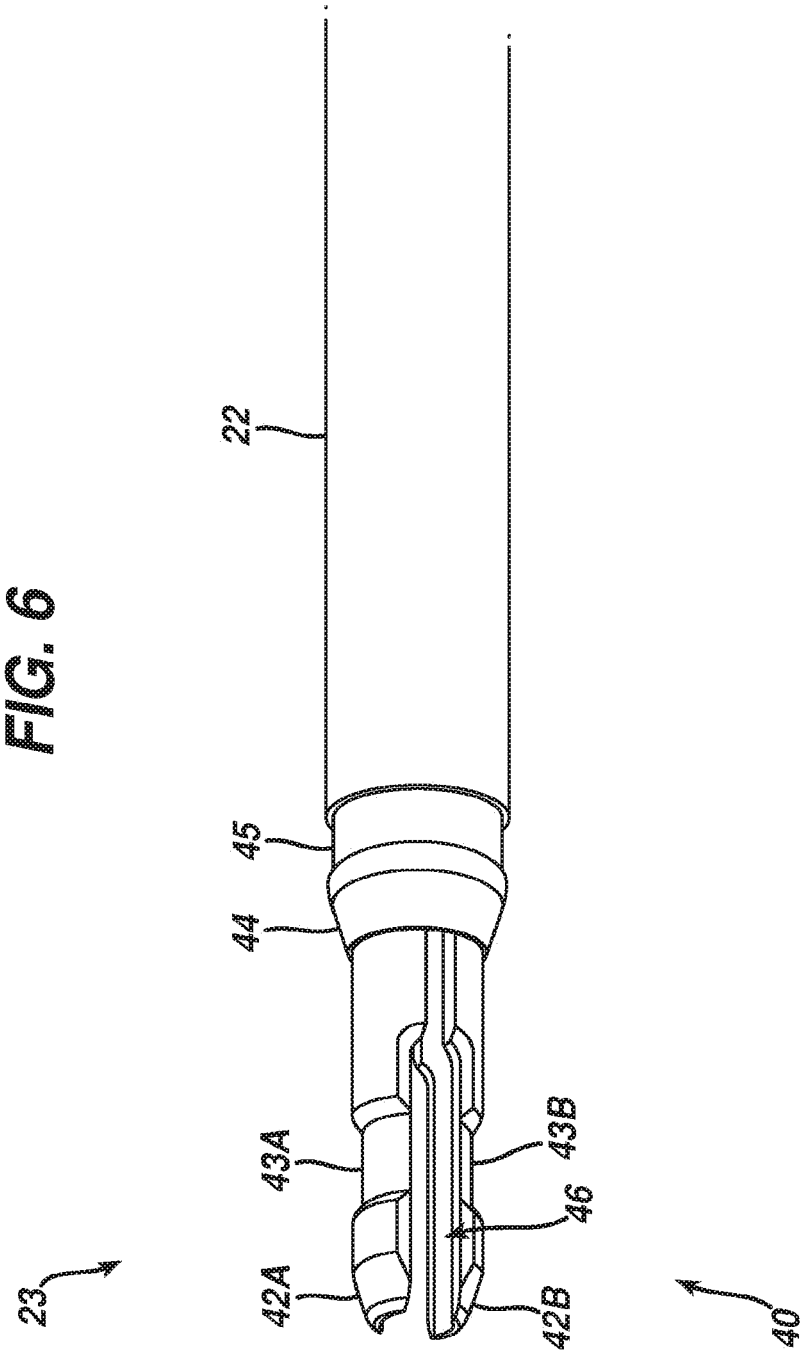

LOADER FOR EXCHANGING END EFFECTORS IN VIVO

CROSS-REFERENCE TO RELATED APPLICATIONS

This application claims priority to U.S. application Ser. No. 12/576,565, filed on Oct. 9, 2009, now U.S. Pat. No. 9,295,485, the entire contents of which is incorporated by reference herein.

BACKGROUND

The present invention relates in general to surgical devices and procedures, and more particularly to minimally invasive surgery.

Surgical procedures are often used to treat and cure a wide range of diseases, conditions, and injuries. Surgery often requires access to internal tissue through open surgical procedures or endoscopic surgical procedures. The term "endoscopic" refers to all types of minimally invasive surgical procedures including laparoscopic, arthroscopic, natural orifice intraluminal, and natural orifice transluminal procedures. Endoscopic surgery has numerous advantages compared to traditional open surgical procedures, including reduced trauma, faster recovery, reduced risk of infection, and reduced scarring. Endoscopic surgery is often performed with an insufflatory fluid present within the body cavity, such as carbon dioxide or saline, to provide adequate space to perform the intended surgical procedures. The insufflated cavity is generally under pressure and is sometimes referred to as being in a state of pneumoperitoneum. Surgical access devices are often used to facilitate surgical manipulation of internal tissue while maintaining pneumoperitoneum. For example, trocars are often used to provide a port through which endoscopic surgical instruments are passed. Trocars generally have an instrument seal, which prevents the insufflatory fluid from escaping while an instrument is positioned in the trocar.

While surgical access devices are known, no one has previously made or used the surgical devices and methods in accordance with the present invention.

BRIEF DESCRIPTION OF DRAWINGS

While the specification concludes with claims which particularly point out and distinctly claim the invention, it is believed the invention will be better understood from the following description taken in conjunction with the accompanying drawings illustrating some non-limiting examples of the invention. Unless otherwise indicated, the figures are not necessarily drawn to scale, but rather to illustrate the principles of the invention.

FIG. 5 depicts an isometric close-up view of the distal end of an instrument in a locked position;

FIG. 6 depicts an isometric close-up view of the distal end of an instrument in an unlocked position;

DETAILED DESCRIPTION

Figure 1:
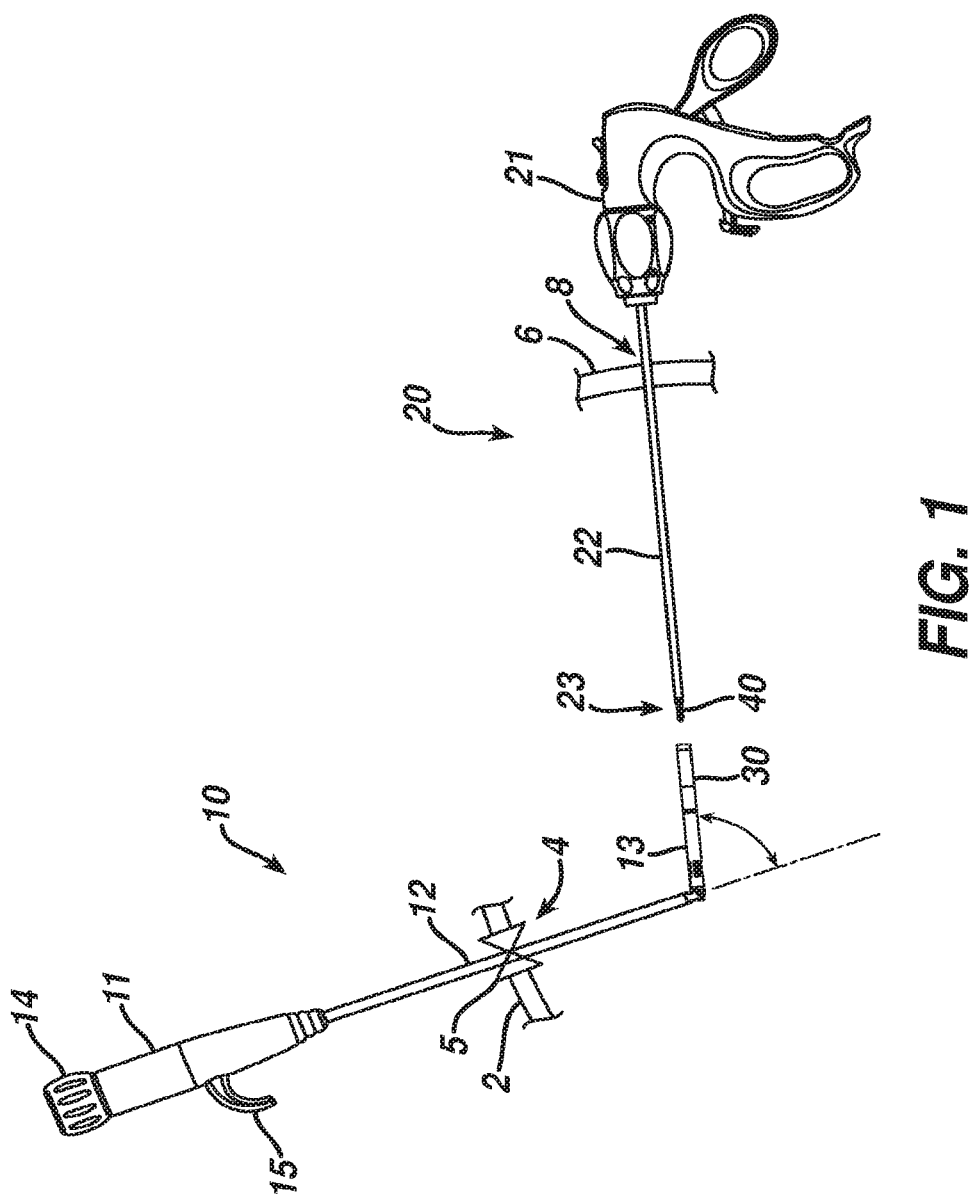
FIG. 1 depicts surgical procedure with an instrument and loader holding an end effector.
Figure 2:
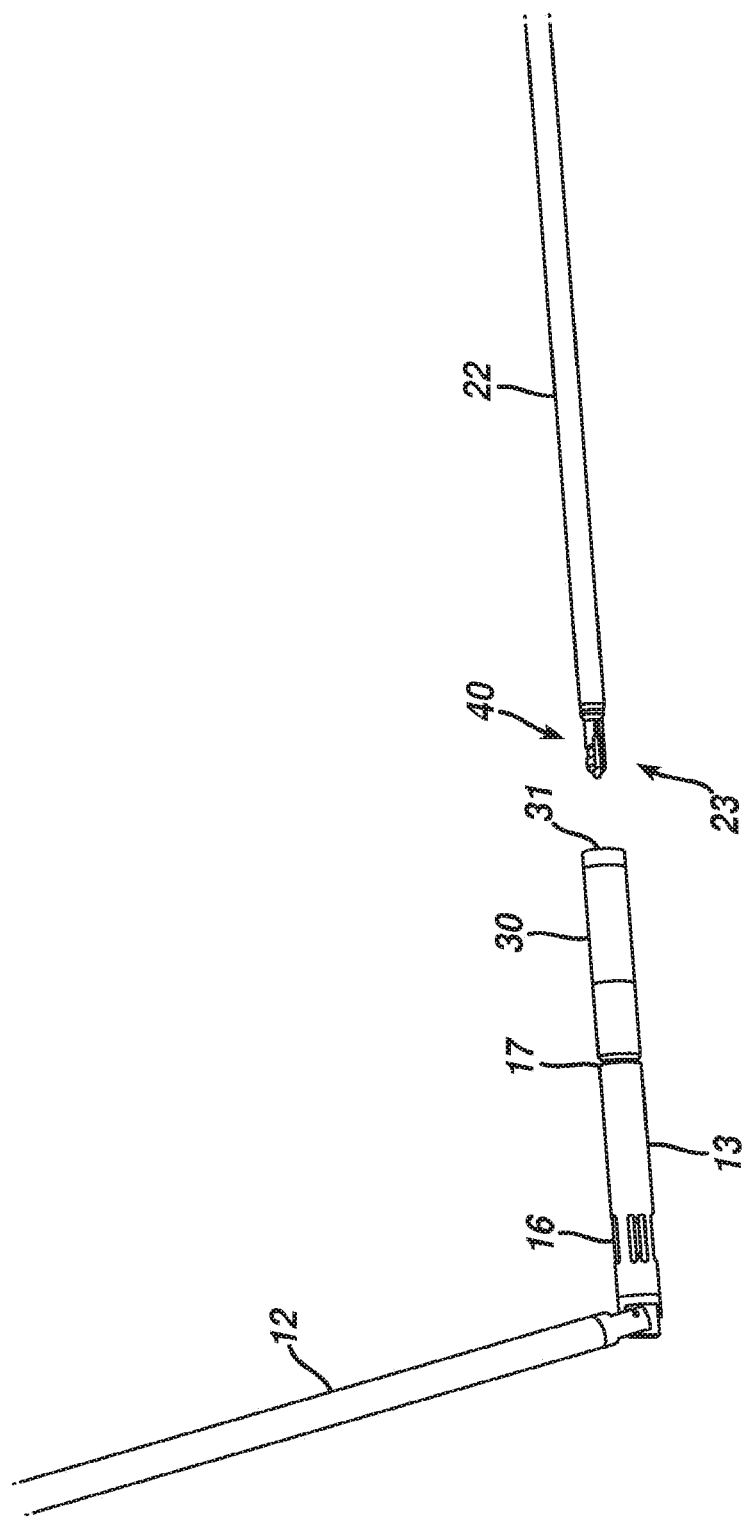
FIG. 2 depicts a close-up view of the distal ends of the instrument and loader in FIG. 1.
Figure 3:
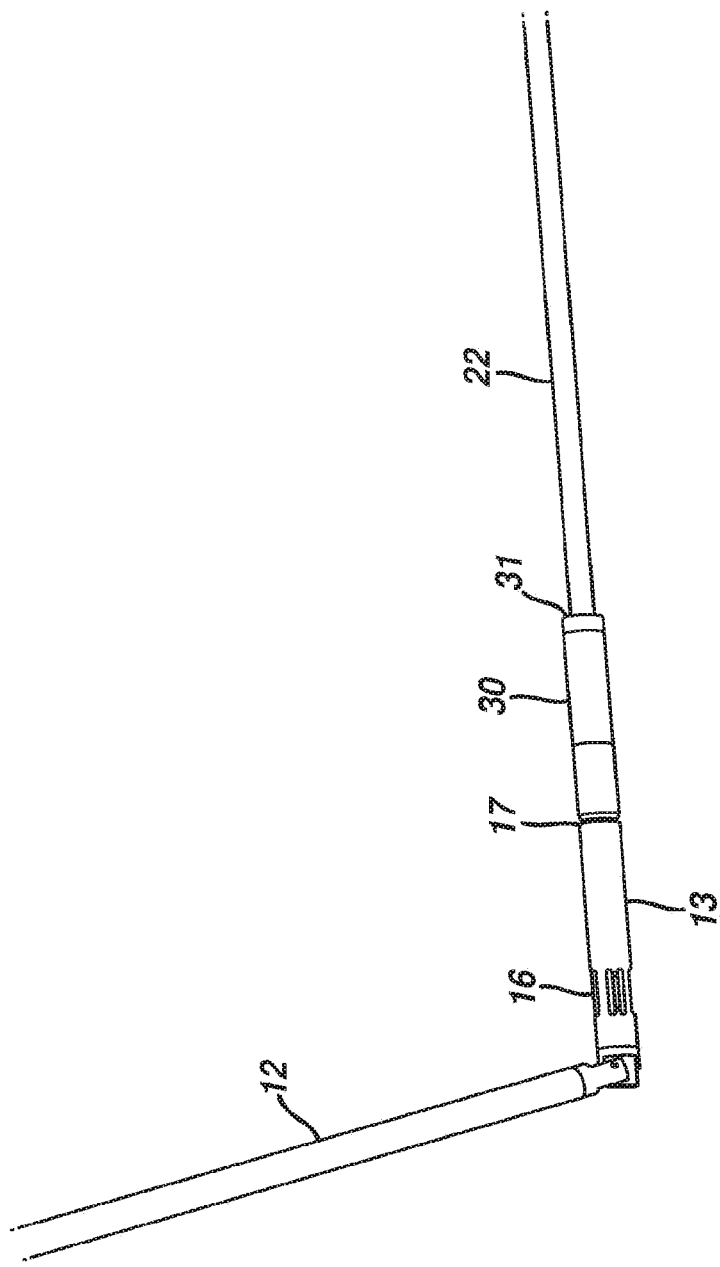
FIG. 3 depicts an instrument being inserted into an end effector.

As shown in FIG. 1, instrument (20) comprises an elongate shaft (22) passing through an incision (8) of a tissue wall (6). A loader (10) comprises an elongate shaft (12) passing through an incision (4) of a tissue wall (2). The surgical end effector (30) is selectively attachable in vivo and detachable in vivo to the attachment mechanism (40) located at the distal end (23) of the instrument (20). In this example, the end effector is a jawed tissue grasper, but a variety of other end effectors could be also be used. The end effector (30) may be loaded ex vivo into the distal end (13) of the shaft (12), and then introduced into the surgical field through the incision (4). The loader (10) holds the end effector (30) during the in vivo attachment to and in vivo detachment from the instrument (20). The loader (10) and instrument (20) each includes ex vivo handles (11, 21) attached to the proximal ends of the shafts (12, 22) that enable surgeons to use the devices.

The tissue wall (2, 6) anatomies will vary based on the surgical procedure, but some non-limiting examples include percutaneous incisions into the abdomen, thorax, or pelvis. The incisions (4, 8) may be created with a cutting or puncturing instrument, and will typically he spaced from one another. The tissue walls (2, 6) may be the same or different anatomies. For instance, tissue walls (2, 6) may both be the abdominal wall. In another example, tissue wall (2) could be an organ (e.g., stomach, colon, esophagus, etc.) accessed through a natural orifice, while the incision (8) in tissue wall (6) could be percutaneous. In yet another example, incision (4) may provide access to the abdomen, while the incision (8) may provide access to the pelvis. If pneumoperitoneum is desired, the incisions may include instrument seals, such as those commonly found in trocars. In this example, the instrument seal (5) is schematically shown in incision (4) with the loader (10) passing through the seal (5), while the shaft (22) seals directly with the tissue wall (6) by virtue of the resilience of the tissue without the aid of a sealing device.

The loader shaft (12) in this embodiment is rigid and straight, but the shaft (12) could be curved or flexible, which would be beneficial for natural orifice transluminal introduction of the distal end (13) to the surgical field. The loader (10) may include an articulating distal end (13) controlled by the knob (14). The distal end (13) will typically be introduced and removed through the incision (4) in-line with the shaft (12), and then articulated in vivo to facilitate alignment between the end effector (30) and the shaft (22). The arm (15) is rigidly connected the handle (11) to facilitate grasping of the handle and rotational orientation of the articulated distal end (13) about the shaft (12) axis. In this embodiment, the distal end (13) of the loader (10) comprises a tube opening at the distal tip (17). The tube is dimensioned to receive the end effector (30). The tube (30) includes an engagement feature (16) for holding the end effector (30). While the engagement feature (16) may vary, in this embodiment a plurality of leaf springs provide an interference fit with the end effector (30) to frictionally hold the end effector in the tube. In this embodiment, when the end effector (30) is loaded in the tube, the distal end (32) is positioned in the tube and the proximal end (31) extends from the tube opening (17). This arrangement prevents the jaws of the end effector from opening. After the distal end (23) of the instrument (20) is attached to the proximal end (31) of the end effector (30), the end effector (3) can be pulled from the distal end (13) of the loader (10).

Figure 4:
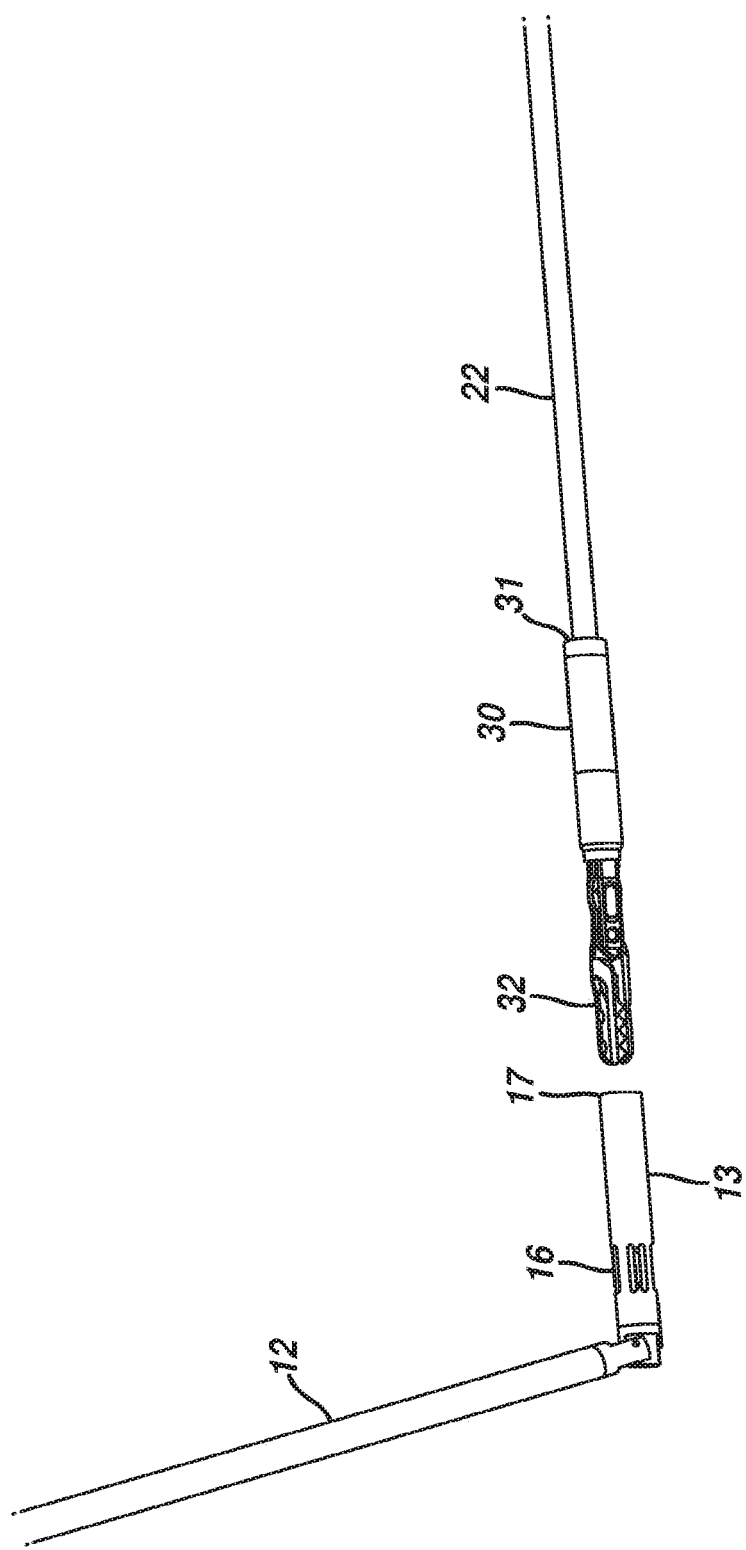
FIG. 4 depicts an instrument attached to an end effector being withdrawn from a loader.
Figure 4A:
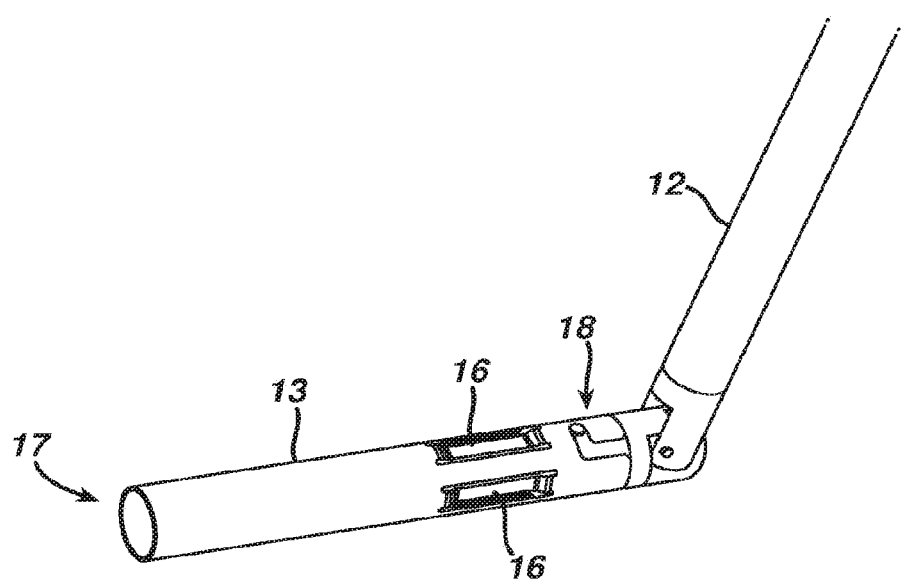
FIG. 4A depicts a loader with removable distal end.

FIG. 4A depicts an alternative embodiment of a loader (10) where the distal end (13) is selectively attachable and detachable to the shaft (12). As shown in this example, this feature is enabled with a bayonet connection (18), but other connections are also contemplated including snap connections, threaded connections, and the like. One advantage of this alternative embodiment is that different distal end (13) configurations may be used to hold end effectors that may not be accommodated by a single sized tube.

FIGS. 5 and 6 depict a detailed view of one embodiment of an attachment mechanism (40) located at the distal end (23) of the shaft (22). The attachment mechanism (40) comprises a mating feature on the shaft (22), which in this embodiment is a circumferential groove (45) positioned on the lateral surface of the shaft (22). The attachment mechanism (40) also comprises arms (42A, 42B) projecting distally from the distal end (44) of the shaft (22). The arms are axially slideable relative the shaft (22) and are resiliently deflectable medially into the gap (46). The arms each comprise a mating feature, which in this embodiment comprises a stepped lateral notch (43A, 43B). An elongate pin (41) is positioned medially relative the arms (42) and is axially slideable relative the arms (42) between a locked position preventing medial deflection of the arms (an example of which is shown in FIG. 5) and an unlocked position allowing medial deflection of the arms (an example of which is shown in FIG. 6). The pin (41) and arms (42) may each slide independently relative the shaft (22).

As shown in the embodiment of FIG. 5, the elongate pin (41) may include a pointed obtruator tip. In this configuration the distal end (23) may be used to puncture through the tissue wall (6). The distal ends of the arms (42) and distal end (44) of the shaft (22) include tapered surfaces to facilitate passing through the incision (8).

Figure 7:
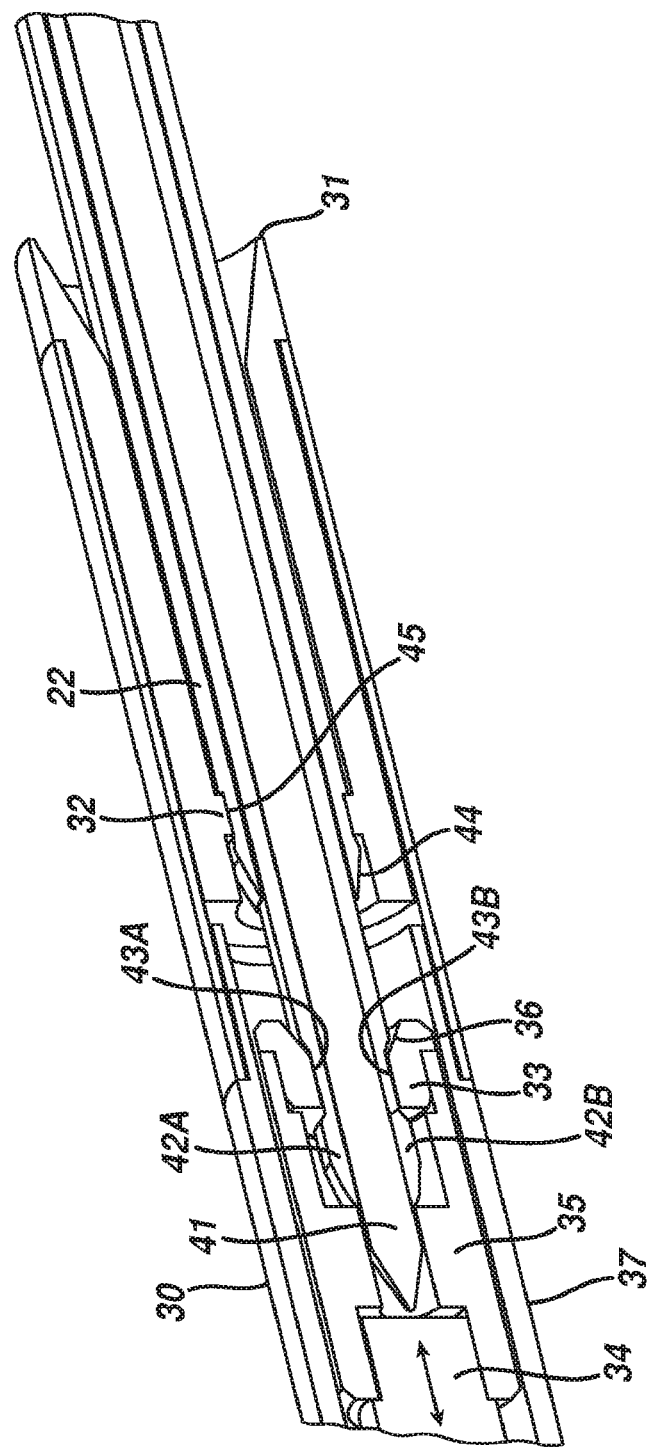
FIG. 7 depicts an isometric cross-sectional view of the distal end of an instrument attached to an end effector.

FIG. 7 shows the attachment mechanism (40) attached to the end effector (30). The groove (45) of the shaft (22) mates the rib (32) of the end effector (30) preventing relative axial motion. The lateral grooves (43) of the arms (42) mate the ring (33) of the end effector (30) preventing relative axial motion. The rib (32) is rigidly connected to the outer housing (37) of the end effector (30), and the ring (33) is rigidly connected to the jaw actuator (34) via the coupling (35). Accordingly, axial movement of the arms (42) relative the shaft (22) will cause axial movement of the jaw actuator (34) relative the housing (37), thereby causing the jaws to open and close.

The following describes one method for attaching the end effector (30) to the shaft (22). The distal end (23) is introduced in into the proximal end (31) of the end effector (30) with the pin (41) in the unlocked position. As the arms (42) are advanced axially into the end effector (30), the chamfered lead (36) of the ring (33) medially deflects the arms (42) until the ring (33) is seated into the lateral notches (43). Simultaneously the shaft (22) advances axially into the end effector (30), and the tapered end (44) aligns the rib (32) to seat into the groove (45). In both cases, the surgeon will feel a tactile "snap" indicating proper engagement. Once fully seated in the end effector (30), the pin (41) may be slid to the locked position thereby attaching the end effector (30) to the instrument (20). Once attached, the surgeon may pull the end effector from the loader (10), and the loader (10) may then be removed from the surgical field. The surgeon may then manipulate tissue with the end effector (30) as needed for the surgical procedure.

Figure 9:
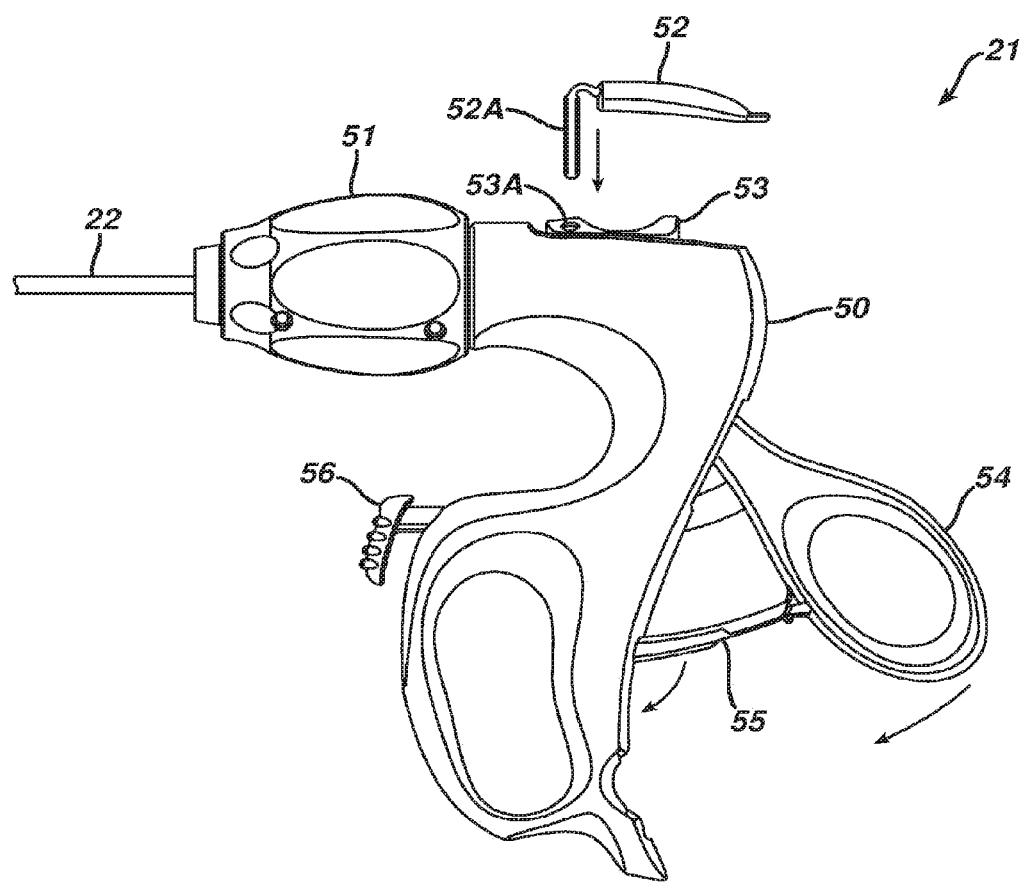
FIG. 9 depicts an instrument handle.
Figure 10:
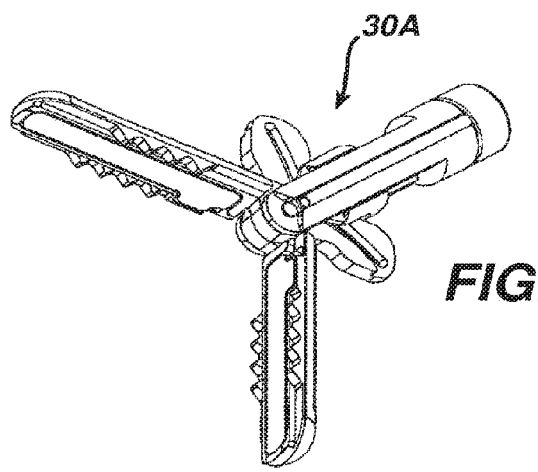
FIG. 10 depicts a bi-polar jawed end effector.
Figure 11:
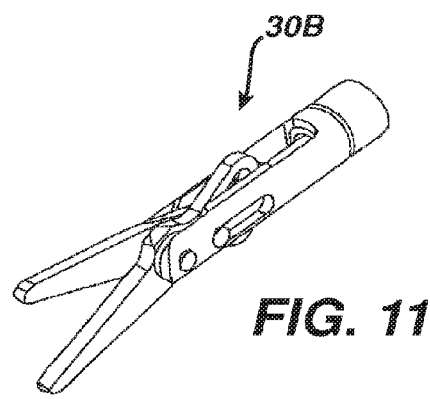
FIG. 11 depicts a cutting shears end effector.
Figure 12:
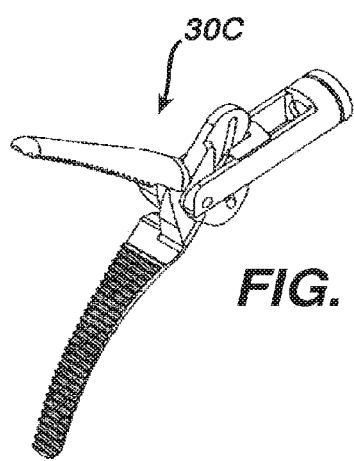
FIG. 12 depicts a Maryland dissector end effector.
Figure 13:
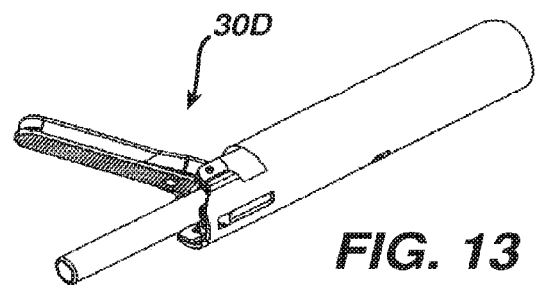
FIG. 13 depicts an ultrasonic shears end effector.

FIG. 9 shows and example of the handle (21) for the instrument (20). The handle (21) includes a base (50). A knob (51) rotates the attachment mechanism (40) about the axis of the shaft (22), which will also rotate an attached end effector (30). The trigger (54) pivots relative the base (50) causing axial movement of the arms (42) and the pin (41) relative the shaft (22). Operation of the trigger (54) will operate the jaws on an attached end effector (30). The latch (55) pivots relative the base (50) between a locked position (as shown in figure) to prevent operation of the trigger (54) and an unlocked position recessed in the base (50). During seating with the end effector (30), the latch (55) may be locked to maintain the same relative axial spacing of the corresponding the mating features (43, 45) as the mating features (33, 32), resulting in resulting in a single "snap" feedback. The trigger lock (56) can lock/unlock the trigger in/from its depressed position. An actuator (53), which in this embodiment is a slider, controls axial movement of the pin (51) relative the arms (42). The distal most position of the actuator (53) relative the base (as shown in the figure) places the pin (51) in its locked position, and the proximal most position places the pin (51) in its unlocked position. The pin lock (52) includes a pin (52A) which went inserted into the hole (53A) maintains the pin (41) and arms (42) in the extended and locked positions as shown in FIG. 5.

FIGS. 10-13 illustrate some non-limiting examples of alternative end effectors (30A-D) that may attached to the distal end (23) of the instrument (20). In addition to the loader (10) and instrument (20), all or a portion of the end effectors (30, 30A, 30B, 30C, 30D) may be bundled as part of a kit so the surgeon may interchange the attached end effector as needed for a surgical procedure. All the end effectors examples shown here have cooperating jaws; however, non-jawed end effectors could also be employed such as hook knives, snares, and the like. In the case of end effectors that require energy, appropriate energy transmission mechanisms known in the art. Should be added to the handle (21) and shaft (22). For instance, appropriate electrical connections can be added for the bi-polar forceps end effector (30A). Similarly, an ultrasonic transducer and waveguide can be added for the ultrasonic shears end effector (30D).

The following describes one method for using the devices during a laparoscopic surgical procedure. An instrument (20) is obtained and passed through incision (8). The incision (8) may be a precutaneous incision formed at least partially by a puncture formed with the obtruator on the pin (41) in the configuration shown in FIG. 5. The pin lock (52) and latch (55) may be secured to the slider (53) and trigger (54), respectively. After the puncture, the pin lock (52) may be removed.

A loader (10) and end effector (30) are obtained. The end effector (30) may be selected from a plurality of end effectors provided in a kit. The end effector (30) is loading ex vivo into the distal end (13) of the loader (10). The distal end (13) of the loader (10) with the loaded end effector (30) is passed through incision (4). The second incision (4) may also be percutaneous incision spaced from the first incision (8), and may include passing the distal end (13) with the loaded end effector (30) through a trocar. The distal end (13)

may be articulated to facilitate orientation between the proximal end (31) of the end effector (30) and the attachment mechanism (40). The actuator (53) is slid proximally to move the pin (41) to its unlocked position. The distal end (23) of the instrument (20) is advanced into the proximal end (31) of the end effector (30) until the respective mating features of the instrument (20) and end effector (30) are engaged. The actuator (53) may then be slid distally thus advancing the pin (41) to its locked position. The end effector (30) has now been attached in vivo to the instrument (20). The end effector (30) may then be pulled from the loader (10) and the latch (55) disengaged from the trigger (54). Tissue is then manipulating by actuating the trigger (54) of the handle (21) to operate the jaws of the end effector (30).

Figure 8:
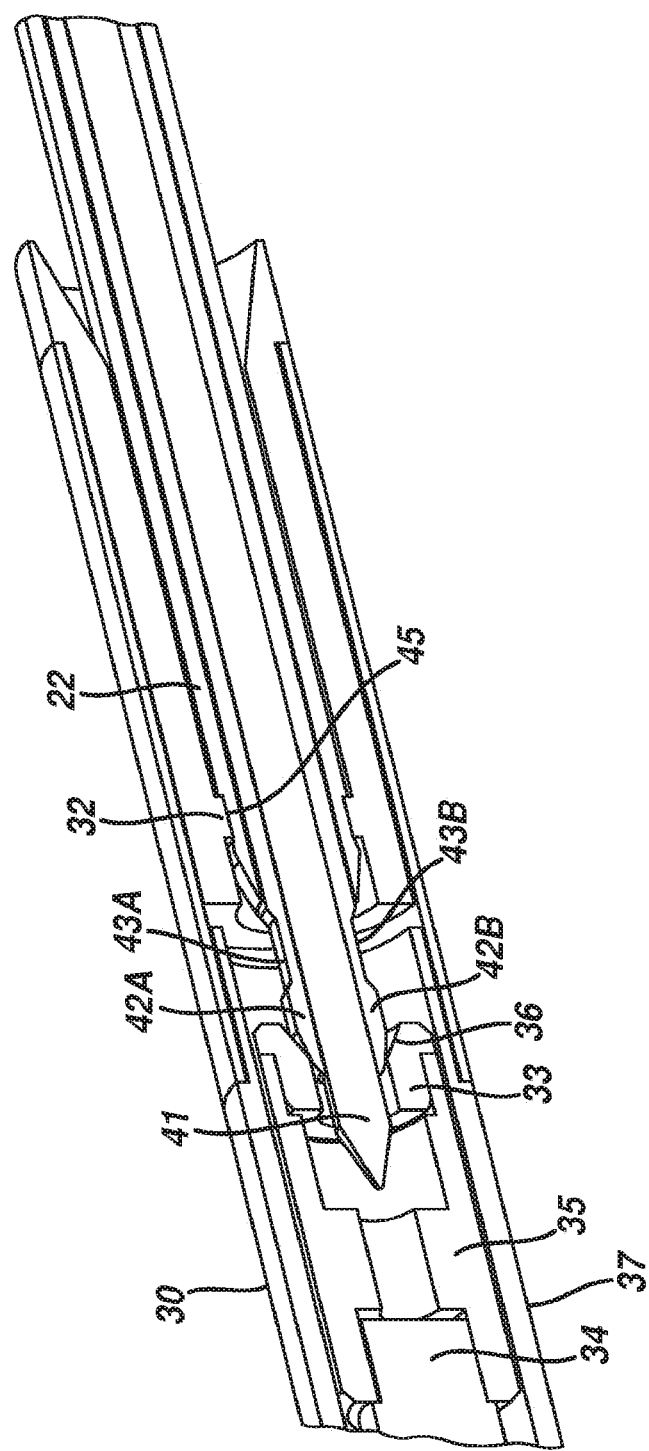
FIG. 8 depicts an isometric cross-sectional view of the distal end of an instrument attached to an end effector in a pushed-off configuration.

After completing the surgical procedure, the end effector (30) may be detached from the shaft (22). if previously removed, the loader (10) may be reintroduced through the incision (4) into the surgical field. The distal end (32) of the end effector (30) is seated into the distal end (13) of the loader (10), and the pin (41) moved to its unlocked position. The arms (42) are then proximally withdrawn from the ring (33) and the pin (41) is returned to the locked position. Accordingly, the device will be in the configuration depicted in FIG. 8. Distally advancing the arms (42) will push the ring (33) distally till the rib (32) unseats from the groove (45). This unseating may be facilitated by the jaws of the end effector (30) being held in a closed position by the tube in the loader distal end (13). The distal end (23) may then he withdrawn from the end effector (30) thus detaching the end effector (30) from the instrument (20). The end effector will be held in the loader (10) by virtue of the engagement feature (16). Removal of the loader (10) from the surgical field will remove the end effector (30). A different end effector may then be attached to the instrument (20), or the instrument (20) may be withdrawn from the surgical field.

Without limitation, the following describe some of the benefits and advantages of the foregoing devices and methods over the prior art. The end effector (30) may have a much larger diameter than the shaft (22); accordingly, the incision (8) can be smaller compared to more traditional laparoscopic instruments resulting in less pain and scarring, and quicker recovery. This also facilitates a small diameter shaft (22) (even less than 3 mm), thus potentially eliminating a trocar in the incision (8). The attachment mechanism (40) provides quick end effector (30) exchanges with the instrument (20), thus decreasing surgical time. The loader (10) also facilitates quick end effector (30) exchanges. A kit of multiple end effectors may reduce instrument costs by consolidating a single shaft (22) and handle (21) for all instruments. Many other benefits will be apparent to those skilled in the art.

Having shown and described various embodiments and examples of the present invention, further adaptations of the methods and devices described herein can be accomplished by appropriate modifications by one of ordinary skill in the art without departing from the scope of the present invention. Several of such potential modifications have been mentioned, and others will be apparent to those skilled in the art. For instance, the specific materials, dimensions, and the scale of drawings will he understood to be non-limiting examples. Accordingly, the scope of the present invention should be considered in terms of the following claims and is understood not to be limited to the details of structure, materials, or acts shown and described in the specification and drawings.

The invention claimed is:

1. A laparoscopic surgical kit, comprising:
a) a first percutaneous instrument comprising an elongate shaft and a first handle, the elongate shaft comprising a distal end and a proximal end, the proximal end being connected to the first handle, the distal end comprising a mating feature, and the handle comprising a knob configured to rotate the mating feature about an axis of the elongate shaft;
b) a surgical end effector selectively attachable in vivo and detachable in vivo to the mating feature of the first percutaneous instrument;
c) a second percutaneous instrument comprising a shaft, a second handle, and a tube, the shaft comprising a distal end and a proximal end, the proximal end being connected to the second handle, the distal end being connected to the tube, the tube being selectively bendable or articulatable at an angle relative to the shaft, the tube comprising a distal opening dimensioned and configured to selectively receive and release the surgical end effector in vivo, and the tube comprising an engagement feature capable of holding the surgical end effector during the in vivo attachment to and in vivo detachment from the first percutaneous instrument.

2. The laparoscopic surgical kit of claim 1, wherein the engagement feature frictionally holds the surgical end effector.

3. The laparoscopic surgical kit of claim 2, wherein the engagement feature comprises one or more leaf springs.

4. The laparoscopic surgical kit of claim 1, comprising a plurality of surgical end effectors each selectively attachable in vivo and detachable in vivo to the mating feature of the first percutaneous instrument.

5. The laparoscopic surgical kit of claim 1, comprising a plurality of surgical end effectors each selectively attachable in vivo and detachable in vivo to the mating feature of the first percutaneous instrument, and each sized to be received by the tube.

6. The laparoscopic surgical kit of claim 1, wherein the distal end of the second percutaneous instrument is selectively attachable and detachable.

* * * * *